United States Patent [19]
Kumar

[11] Patent Number: 6,022,495
[45] Date of Patent: Feb. 8, 2000

[54] PHOTOCHROMIC BENZOPYRANO-FUSED NAPHTHOPYRANS

[75] Inventor: Anil Kumar, Pittsburgh, Pa.

[73] Assignee: Transitions Optical, Inc., Pinellas Park, Fla.

[21] Appl. No.: 09/114,089

[22] Filed: Jul. 10, 1998

[51] Int. Cl.[7] ............................. G02B 5/23; C07D 311/78
[52] U.S. Cl. ......................... 252/586; 549/382; 549/58; 549/60; 549/337; 549/362; 544/124; 544/148; 544/150; 546/167; 546/194; 546/196; 546/197; 546/280.7; 546/281.1; 546/284.1; 548/454; 548/518; 548/525; 548/526
[58] Field of Search .............................. 252/586; 549/382, 549/58, 60, 337, 362; 544/124, 148, 150; 546/167, 194, 196, 197, 280.7, 281.1, 284.1; 548/454, 518, 525, 526

[56] References Cited

U.S. PATENT DOCUMENTS

| | | | |
|---|---|---|---|
| 3,567,605 | 3/1971 | Becker | 204/158 |
| 3,627,690 | 12/1971 | Casella et al. | 252/300 |
| 4,818,096 | 4/1989 | Heller et al. | 351/163 |
| 5,066,818 | 11/1991 | Van Gemert et al. | 549/389 |
| 5,429,774 | 7/1995 | Kumar | 549/383 |
| 5,458,814 | 10/1995 | Kumar et al. | 252/586 |
| 5,514,817 | 5/1996 | Knowles | 252/586 |
| 5,552,091 | 9/1996 | Kumar | 252/586 |
| 5,565,147 | 10/1996 | Knowles et al. | 252/586 |
| 5,645,767 | 7/1997 | Van Gemert | 252/586 |
| 5,651,923 | 7/1997 | Kumar et al. | 252/586 |
| 5,674,432 | 10/1997 | Knowles et al. | 252/586 |
| 5,723,072 | 3/1998 | Kumar | 252/586 |
| 5,869,658 | 2/1999 | Lin et al. | 252/586 |

*Primary Examiner*—Philip Tucker
*Attorney, Agent, or Firm*—Frank P. Mallak; Irwin M. Stein

[57] ABSTRACT

Described are novel photochromic benzopyrano-fused naphthopyran compounds, examples of which are naphthopyran compounds having a substituted or unsubstituted benzopyran group fused to one side of the naphtho portion of the naphthopyran and having certain substituents at the position ortho to the oxygen atom of the naphthopyran ring. These compounds may be represented by the following graphic formulae:

Also described are polymeric organic host materials that contain or that are coated with such compounds or combinations thereof with complementary photochromic compounds, e.g., certain other naphthopyrans, nenzopyrans, and spiro(indoline)type compounds.

22 Claims, No Drawings

PHOTOCHROMIC BENZOPYRANO-FUSED NAPHTHOPYRANS

DESCRIPTION OF THE INVENTION

The present invention relates to certain novel naphthopyran compounds. More particularly, this invention relates to novel photochromic benzopyrano-fused naphthopyran compounds and to compositions and articles containing such novel naphthopyran compounds. When exposed to electromagnetic radiation containing ultraviolet rays, such as the ultraviolet radiation in sunlight or the light of a mercury lamp, many photochromic compounds exhibit a reversible change in color. When the ultraviolet radiation is discontinued, such a photochromic compound will return to its original color or colorless state. Various classes of photochromic compounds have been synthesized and suggested for use in applications in which a sunlight-induced reversible color change or darkening is desired. U.S. Pat. No. 3,567,605 (Becker) describes a series of pyran derivatives, including certain benzopyrans and naphthopyrans. These compounds are described as derivatives of chromene and are reported to undergo a color change, e.g., from colorless to yellow-orange, on irradiation by ultraviolet light at temperatures below about −30° C. Irradiation of the compounds with visible light or upon raising the temperature to above about 0° C. is reported to reverse the coloration to a colorless state.

U.S. Pat. No. 5,066,818 describes various 3,3-diaryl-3H-naphtho[2,1-b]pyrans as having desirable photochromic properties, i.e., high colorability and acceptable fade, for ophthalmic and other applications. Also disclosed by way of comparative example in the '818 patent are the isomeric 2,2-diaryl-2H-naphtho[1,2-b]pyrans, which are reported to require unacceptably long periods of time to fade after activation.

U.S. Pat. No. 3,627,690 describes photochromic 2,2-di-substituted-2H-naphtho[1,2-b]pyran compositions containing minor amounts of either a base or weak-to-moderate strength acid. The addition of either an acid or base to the naphthopyran composition is reported to increase the fade rate of the colored naphthopyrans, thereby making them useful in eye protection applications such as sunglasses. It is reported therein further that the fade rate of 2H-naphtho-[1,2-b]pyrans without the aforementioned additives ranges from several hours to many days to reach complete reversion.

U.S. Pat. No. 4,818,096 discloses purple/blue coloring photochromic benzo- or naphthopyrans having at the position alpha to the oxygen of the pyran ring a phenyl group having a nitrogen containing substituent in the ortho or para positions. U.S. Pat. No. 5,645,767 describes novel photochromic indeno-fused 2H-naphtho[1,2-b]pyran compounds, the 2,1-positions of the indeno group being fused to the f side of the naphthopyran.

U.S. Pat. No. 5,458,814 discloses photochromic 2H-naphtho[1,2-b]pyran compounds having certain substituents at the number 5 and 6 carbon atoms of the naphtho portion of the naphthopyran and at the 2-position of the pyran ring. These compounds have an acceptable fade rate in addition to a high activated intensity and a high coloration rate.

The present invention relates to novel substituted naphtho[1,2-b]pyran compounds having a substituted or unsubstituted benzopyrano group fused to the f side of the naphtho portion of the naphthopyran, which compounds may be represented by graphic formulae Ia and Ib hereinafter; and substituted naphtho[2,1-b]pyran compounds having a substituted or unsubstituted benzopyran group fused to the i or l side of the naphtho portion of the naphthopyran, which compounds may be represented by graphic formulae Ic and Id hereinafter. All of these compounds have certain substituents at the position ortho to the oxygen atom of the naphthopyran. These compounds have demonstrated an acceptable fade rate without the addition of acids or bases, a high activated intensity and a high coloration rate.

DETAILED DESCRIPTION OF THE INVENTION

In recent years, photochromic plastic materials, particularly plastic materials for optical applications, have been the subject of considerable attention. In particular, photochromic ophthalmic plastic lenses have been investigated because of the weight advantage they offer, vis-a-vis, glass lenses. Moreover, photochromic transparencies for vehicles, such as cars and airplanes, have been of interest because of the potential safety features that such transparencies offer.

In accordance with the present invention, it has now been discovered that certain novel dihydro[2]benzopyrano[3',4':3,4]naphtho[1,2-b]pyrans, dihydro[1]benzopyrano[3',4':3,4]naphtho[1,2-b]pyrans, dihydro[2]benzopyrano[4',3':3,4]naphtho[2,1-b]pyrans and dihydro[2]benzopyrano[3',4':5,6]naphtho[2,1-b]pyrans having activated colors ranging from red to purple, an acceptable fade rate, high activated intensity and a high coloration rate may be prepared. These compounds may be described as benzopyrano-fused naphthopyrans having certain substituents at the position ortho to the oxygen atom of the naphthopyran ring. In particular, the compounds include 6,10-dihydro[2]benzopyrano[3',4':3,4]naphtho[1,2-b]pyrans and 6,9-dihydro[1]benzopyrano[3',4':3,4]naphtho[1,2-b]pyrans having certain substituents at the number 10 and 9 positions, respectively. Certain substituents may also be present at the number 1, 2, 3, 4, 11, 12, 13 or 14 carbon atoms of the compounds.

The invention further includes benzopyrano-fused[2,1-b]naphthopyrans having certain substituents at the position ortho to the oxygen atom of the naphthopyran ring. These compounds are 2,10-dihydro[2]benzopyrano[4',3':3,4]naphtho-[2,1-b]-pyrans having certain substituents at the number 10 position with certain other substituents optionally present at the number 5, 6, 7, 8, 11, 12, 13 and 14 positions. Also included in the invention are 3,8-dihydro[2]benzopyrano[3',4':5,6]-naphtho[2,1-b]pyrans having certain substituents at the number 8 position with certain other substituents optionally present at the number 5, 6, 9, 10, 11, 12, 13 and 14 positions.

These aforedescribed compounds may be represented by the following graphic formulae Ia, Ib, Ic and Id in which the letters a through n represent the sides of the naphthopyran, and the numbers 1 through 14 inside the rings identify the numbering sequence of the ring atoms of the benzopyrano-fused naphthopyran. In the definition of the substituents shown in graphic formulae Ia, Ib, Ic and Id, like symbols have the same meaning unless stated otherwise.

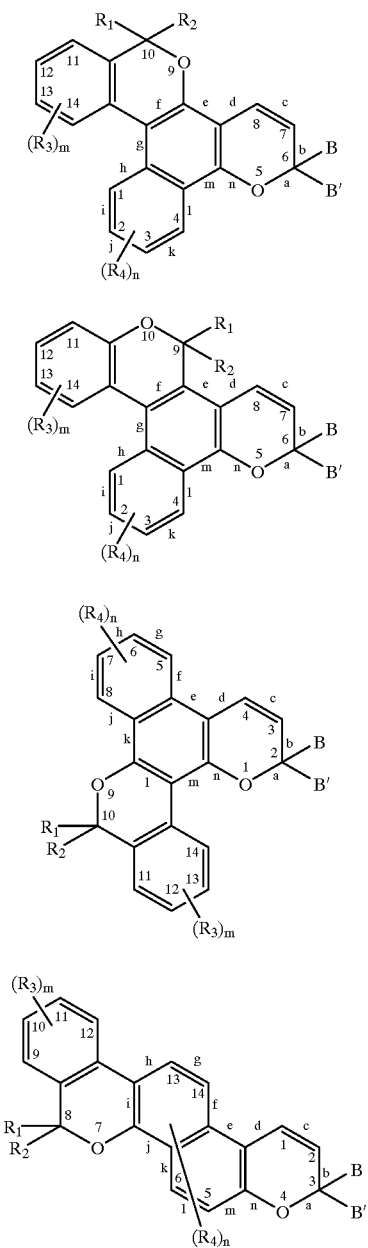

In graphic formulae Ia, Ib, Ic and Id, $R_1$ and $R_2$ may together form an oxo group or $R_1$ and $R_2$ may each be hydrogen, $C_1$–$C_6$ alkyl, $C_3$–$C_7$ cycloalkyl, allyl, phenyl, mono- and di-substituted phenyl, benzyl or mono-substituted benzyl. Each of the phenyl and benzyl group substituents may be $C_1$–$C_6$ alkyl or $C_1$–$C_6$ alkoxy. Preferably, $R_1$ and $R_2$ are each selected from the group consisting of hydrogen, $C_1$–$C_4$ alkyl, $C_3$–$C_6$ cycloalkyl, phenyl, mono- or di-substituted phenyl, benzyl and mono-substituted benzyl. Each of the preferred phenyl and benzyl group substituents are $C_1$–$C_4$ alkyl or $C_1$–$C_4$ alkoxy. More preferably, $R_1$ and $R_2$ are each selected from the group consisting of hydrogen, $C_1$–$C_3$ alkyl, $C_3$–$C_5$ cycloalkyl, phenyl, mono- and di-substituted phenyl, benzyl and mono-substituted benzyl, each of such phenyl and benzyl group substituents being $C_1$–$C_3$ alkyl or $C_1$–$C_3$ alkoxy.

In graphic formulae Ia, Ib, Ic and Id, each $R_3$ and $R_4$ may be selected from the group consisting of $C_1$–$C_6$ alkyl, $C_1$–$C_6$ alkoxy, chloro and fluoro, and m and n are each the integer 0, 1 or 2. Preferably, each $R_3$ and $R_4$ are selected from the group consisting of $C_1$–$C_4$ alkyl, $C_1$–$C_4$ alkoxy and fluoro, and m and n are each the integer 0, 1, or 2. More preferably, $R_3$ and $R_4$ are selected from the group consisting of $C_1$–$C_3$ alkyl and $C_1$–$C_3$ alkoxy and m and n are each the integer 0, 1 or 2.

B and B' in graphic formulae Ia, Ib, Ic and Id may each be selected from the group consisting of:

(i) the unsubstituted, mono-, di- and tri-substituted aryl groups, phenyl and naphthyl;

(ii) the unsubstituted, mono- and di-substituted heteroaromatic groups pyridyl, furanyl, benzofuran-2-yl, benzofuran-3-yl, thienyl, benzothien-2-yl, benzothien-3-yl, each of said aryl and heteroaromatic substituents in parts (i) and (ii) being selected from the group consisting of phenyl, phenyl($C_1$–$C_3$) alkyl, di($C_1$–$C_6$) alkylamino, piperidino, morpholino, pyrryl, $C_1$–$C_6$ alkyl, $C_1$–$C_6$ chloroalkyl, $C_1$–$C_6$ fluoroalkyl, $C_1$–$C_6$ alkoxy, mono($C_1$–$C_6$)alkoxy($C_1$–$C_4$)alkyl, acryloxy, methacryloxy, chloro and fluoro;

(iii) the groups represented by the following graphic formulae:

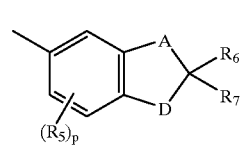

IIA

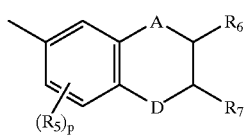

IIB wherein A may be carbon or oxygen and D may be oxygen or substituted nitrogen, provided that when D is substituted nitrogen, A is carbon, said nitrogen substituents being selected from the group consisting of hydrogen, $C_1$–$C_6$ alkyl and $C_2$–$C_6$ acyl; each $R_5$ is $C_1$–$C_6$ alkyl, $C_1$–$C_6$ alkoxy, hydroxy, chloro or fluoro; $R_6$ and $R_7$ are each hydrogen or $C_1$–$C_6$ alkyl; and p is the integer 0, 1 or 2;

(iv) $C_1$–$C_6$ alkyl, $C_1$–$C_6$ chloroalkyl, $C_1$–$C_6$ fluoroalkyl, $C_1$–$C_6$ alkoxy($C_1$–$C_4$)alkyl, $C_3$–$C_6$ cycloalkyl, mono($C_1$–$C_6$)alkoxy($C_3$–$C_6$)cycloalkyl, mono($C_1$–$C_6$)alkyl($C_3$–$C_6$)cycloalkyl, chloro($C_3$–$C_6$)cycloalkyl and fluoro($C_3$–$C_6$)cycloalkyl; and (v) the group represented by the following graphic formula:

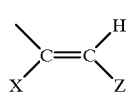

IIC wherein X in graphic formula IIC may be hydrogen or $C_1$–$C_4$ alkyl and Z in graphic formula IIC may be selected from the unsubstituted, mono-, and di-substituted members of the group consisting of naphthyl, phenyl, furanyl and thienyl, each of said group substituents in this part (v) being $C_1$–$C_4$ alkyl, $C_1$–$C_4$ alkoxy, fluoro or chloro; or (vi) B and B' taken together form fluoren-9-ylidene, mono-, or di-substituted fluoren-9-ylidene or form a member selected from the group consisting of saturated $C_3$–$C_{12}$ spiro-monocyclic hydrocarbon rings, e.g., cyclopropylidene, cyclobutylidene, cyclopentylidene, cyclohexylidene, cycloheptylidene, cyclooctylidene, cyclononylidene, cyclodecylidene, cycloundecylidene, cyclododecylidene; saturated $C_7$–$C_{12}$ spirobicyclic hydrocarbon rings, e.g., bicyclo[2.2.1]heptylidene, i.e., norbornylidene, 1,7,7-trimethyl bicyclo[2.2.1] heptylidene, i.e., bornylidene, bicyclo[3.2.1] octylidene, bicyclo[3.3.1]nonan-9-ylidene, bicyclo [4.3.2]undecane, and saturated $C_7$–$C_{12}$ spiro-tricyclic hydrocarbon rings, e.g., tricyclo[2.2.1.0$^{2,6}$]heptylidene, tricyclo[3.3.1.1$^{3,7}$]decylidene, i.e., adamantylidene, and tricyclo[5.3.1.1$^{2,6}$]dodecylidene, each of said fluoren-9-ylidene substituents being selected from the group consisting of $C_1$–$C_4$ alkyl, $C_1$–$C_4$ alkoxy, fluoro and chloro.

More preferably, B and B' are each selected from the group consisting of:

(i) phenyl, mono-substituted phenyl and di-substituted phenyl;

(ii) the unsubstituted, mono- and di-substituted heteroaromatic groups furanyl, benzofuran-2-yl, thienyl and benzothien-2-yl, each of said phenyl and heteroaromatic substituents being selected from the group consisting of di($C_1$–$C_3$)alkylamino, piperidino, morpholino, pyrryl, $C_1$–$C_3$ alkyl, $C_1$–$C_3$ chloroalkyl, $C_1$–$C_3$ fluoroalkyl, $C_1$–$C_3$ alkoxy, mono($C_1$–$C_3$)alkoxy ($C_1$–$C_3$)alkyl, fluoro and chloro;

(iii) the groups represented by the graphic formulae IIA and IIB, wherein A is carbon and D is oxygen, $R_5$ is $C_1$–$C_3$ alkyl or $C_1$–$C_3$ alkoxy, $R_6$ and $R_7$ are each hydrogen or $C_1$–$C_4$ alkyl, and p is the integer 0 or 1;

(iv) $C_1$–$C_4$ alkyl; and (v) the group represented by the graphic formula IIC wherein X is hydrogen or methyl and Z is phenyl or mono-substituted phenyl, said phenyl substituent being selected from the group consisting of $C_1$–$C_3$ alkyl, $C_1$–$C_3$ alkoxy and fluoro; or (vi) B and B' taken together form fluoren-9-ylidene, mono-substituted fluoren-9-ylidene or a member selected from the group consisting of saturated $C_3$–$C_8$ spiro-monocyclic hydrocarbon rings, saturated $C_7$–$C_{10}$ spiro-bicyclic hydrocarbon rings, and saturated $C_7$–$C_{10}$ spiro-tricyclic hydrocarbon rings, said fluoren-9-ylidene substituent being selected from the group consisting of $C_1$–$C_3$ alkyl, $C_1$–$C_3$ alkoxy, fluoro and chloro.

Most preferably, B and B' are each selected from the group consisting of:

(i) phenyl, mono- and di-substituted phenyl;

(ii) the unsubstituted, mono- and di-substituted heteroaromatic groups furanyl, benzofuran-2-yl, thienyl and benzothien-2-yl, each of said phenyl and heteroaromatic substituents being selected from the group consisting of $C_1$–$C_3$ alkyl, $C_1$–$C_3$ alkoxy and fluoro; and (iii) the group represented by graphic formula IIA, wherein A is carbon and D is oxygen, $R_5$ is $C_1$–$C_3$ alkyl or $C_1$–$C_3$ alkoxy, $R_6$ and $R_7$ are each hydrogen or $C_1$–$C_3$ alkyl, and p is the integer 0 or 1; or (iv) B and B' taken together form fluoren-9-ylidene, adamantylidene, bornylidene, norbornylidene, or bicyclo[3.3.1]nonan-9-ylidene.

Compounds represented by graphic formula Ia and Ic may be prepared by the following steps. Benzophenones represented by graphic formula V and VA are either purchased or prepared by Friedel-Crafts methods using an appropriately substituted or unsubstituted benzoyl chloride of graphic formula IV and a commercially available substituted or unsubstituted benzene compound of graphic formula III. See the publication *Friedel-Crafts and Related Reactions*, George A. Olah, Interscience Publishers, 1964, Vol. 3, Chapter XXXI (Aromatic Ketone Synthesis), and "Regioselective Friedel-Crafts Acylation of 1,2,3,4-Tetrahydroquinoline and Related Nitrogen Heterocycles: Effect on NH Protective Groups and Ring Size" by Ishihara, Yugi et al, J. Chem. Soc., Perkin Trans. 1, pages 3401 to 3406, 1992.

The compounds represented by graphic formulae III and IV are dissolved in a solvent, such as carbon disulfide or methylene chloride, and reacted in the presence of a Lewis acid, such as aluminum chloride or tin tetrachloride, to form the corresponding substituted benzophenone represented by graphic formula V (or VA in Reaction B). R and R' represent potential phenyl substituents, as described hereinbefore.

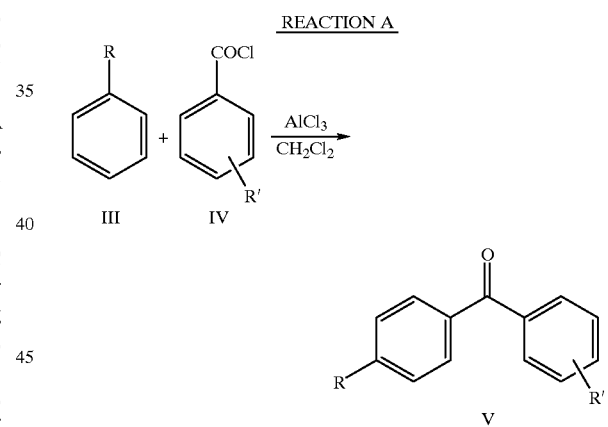

In Reaction B, the substituted or unsubstituted ketone represented by graphic formula VA, in which B and B' may represent groups other than substituted or unsubstituted phenyl, is reacted with sodium acetylide in a suitable solvent, such as anhydrous tetrahydrofuran (THF), to form the corresponding propargyl alcohol represented by graphic formula VI. Propargyl alcohols having B or B' groups other than substituted and unsubstituted phenyl may be prepared from commercially available ketones or for example, from ketones prepared via reaction of an acyl halide with a substituted or unsubstituted benzene, naphthalene, or heteroaromatic compound. Propargyl alcohols having B or B' groups represented by graphic formula IIC may be prepared by the methods described in U.S. Pat. No. 5,274,132, column 2, lines 40 to 68.

REACTION B

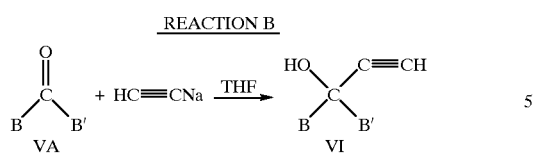

Naphthols represented by graphic formulae IX and X, used in the preparation of naphthopyrans of graphic formula Ia and Ic, respectively, may be prepared as described in Reactions C, D and E. In Reaction C, a substituted 1,3-dihydroxy-naphthalene represented by graphic formula VII is reacted with an o-bromobenzoic acid represented by graphic formula VIII in the presence of copper sulfate with an aqueous alkali, e.g., sodium hydroxide, to produce a mixture of the 8-hydroxy-5H-dibenzo[c,f]chromene-5-one represented by graphic formula IX and the 11-hydroxy-6H-dibenzo[c,h]chromene-6-one represented by graphic formula X.

REACTION C

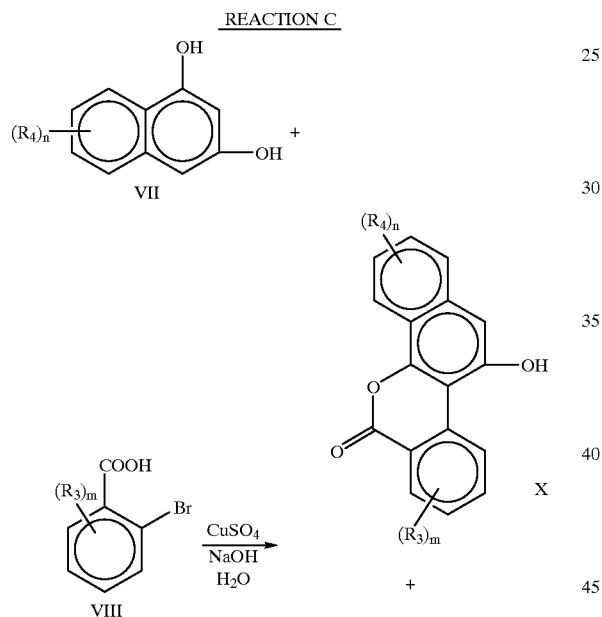

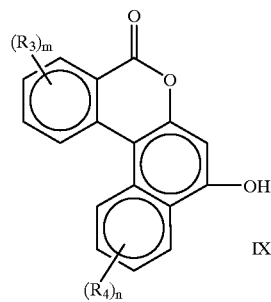

In Reaction D, the compounds represented by graphic formulae IX and X from the mixture produced in Reaction C are each coupled with the propargyl alcohol represented by graphic formula VI in the presence of a catalytic amount of an acid, e.g., p-toluene sulfonic acid in suitable solvent such as chloroform to produce the chromeno-fused naphthopyrans represented by graphic formulae XI and XII.

REACTION D

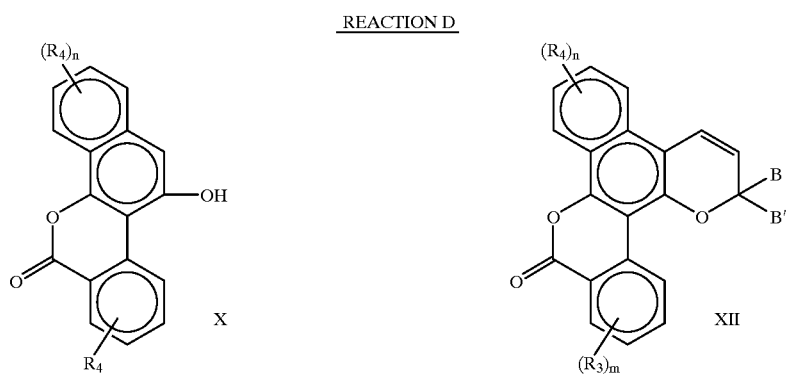

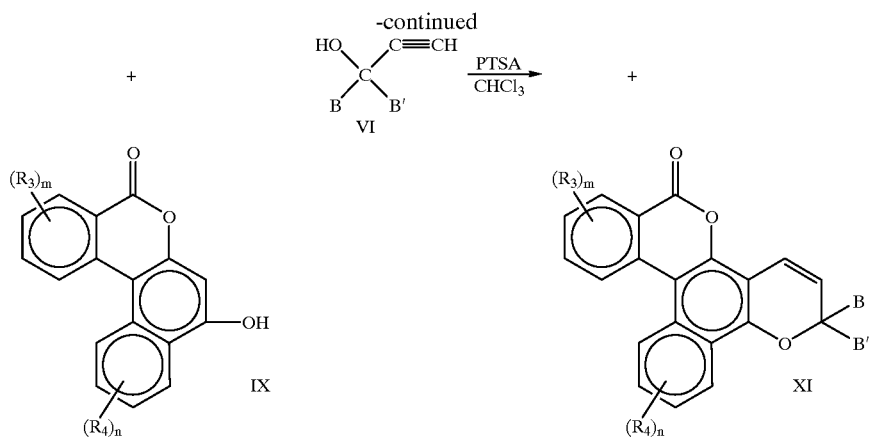

In Reaction E, the compounds represented by graphic formula XI may be reduced, for example, with lithium aluminum hydride (LAH) in an inert solvent such as tetrahydrofuran (THF) to give compounds represented by graphic XIII. Alternatively, the oxo group of compound XI may be reacted with a Grignard reagent (R"MgX) to produce the substituted chromeno-fused naphthopyran of graphic formula XIV.

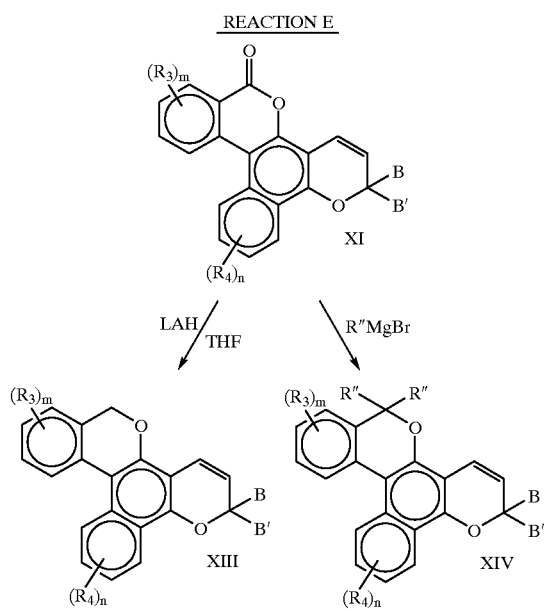

Likewise, the compounds represented by graphic formula XII may be reacted in a similar manner as described in Reaction E either to reduce the oxo group (e.g., with LAH) or to produce substituents in place of the oxo group using a Grignard reagent.

In Reactions F, G and H, methods for preparing compounds represented by graphic formula Ib are described. In Reaction F, o-bromophenol represented by graphic formula XV is reacted with tetrahydropyran (THP) represented by graphic formula XVI in the presence of a catalytic amount of pyridinium para-toluene sulfonate (PPTS) in a suitable solvent such as methylene chloride to produce the THP-protected bromophenol represented by graphic formula XVII. Compound XVII is reacted with magnesium turnings in a suitable solvent such as tetrahydrofuran (THF) in the presence of an initiator, e.g., dibromoethane, yielding the THP-protected ortho-phenol magnesium bromide represented by graphic formula XVIII.

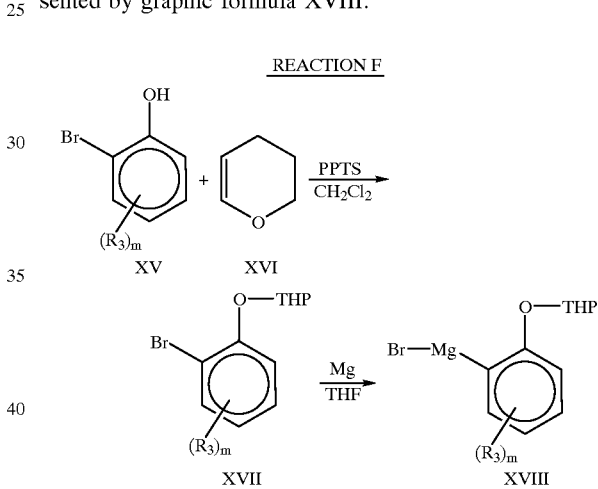

In Reaction G, compound XVIII is reacted with the naphthopyran represented by graphic formula XIX (produced according to the methods described in U.S. Pat. No. 5,458,814, incorporated herein by reference) in a suitable solvent such as tetrahydrofuran, to produce the chromeno-fused naphthopyrans represented by graphic formula XX and the hydroxyphenyl substituted naphthopyrans represented by graphic formula XXI. The desired compound, represented by graphic formula XX, is separated from compound XXI.

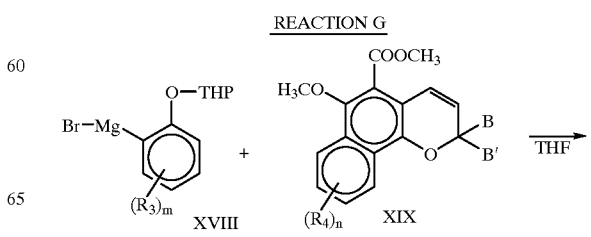

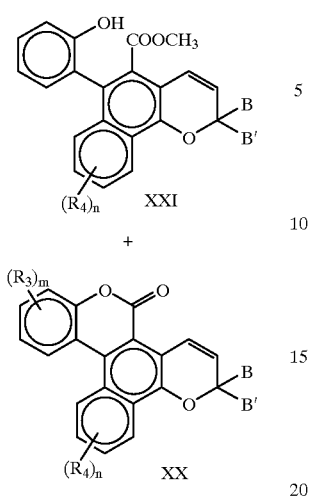

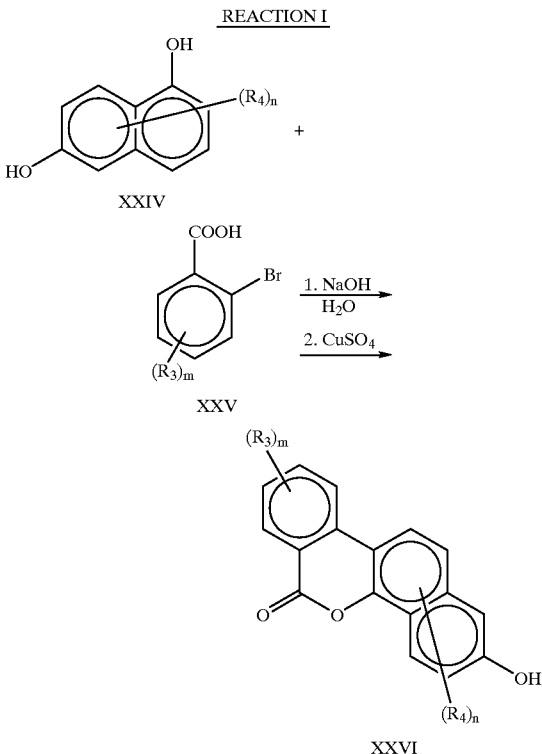

In Reaction H, the compounds represented by graphic formula XX may be reduced, for example, with lithium aluminum hydride (LAH) in an inert solvent such as tetrahydrofuran (THF) to give compounds represented by graphic formula XXII. Alternatively, the oxo group of compound XX may be reacted with a Grignard reagent (R″MgX) to produce the substituted chromeno-fused naphthopyran of graphic formula XXIII.

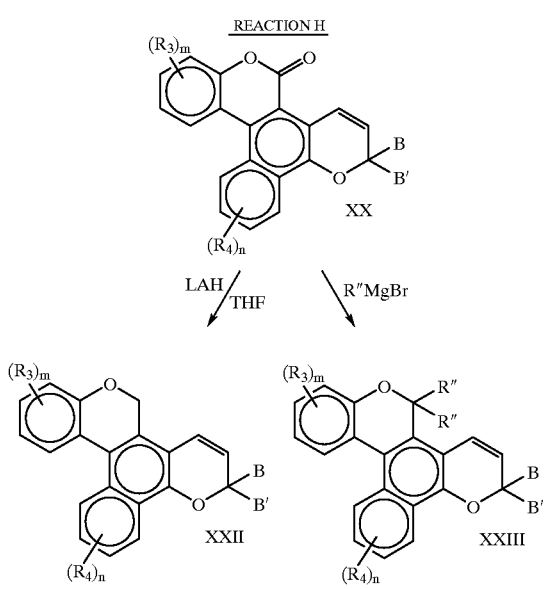

Compounds represented by graphic formula Id may be prepared by the following steps. In Reaction I, 1,6-dihydroxynaphthalene represented by graphic formula XXIV is reacted with 2-bromobenzoic acid represented by graphic formula XXV in the presence of an aqueous alkali, e.g., sodium hydroxide, followed by copper sulfate to produce the naphthol represented by graphic formula XXVI.

In Reaction J, the naphthol represented by graphic formula XXVI is coupled with the propargyl alcohol represented by graphic formula VI in the presence of a catalytic amount of an acid, e.g., p-toluene sulfonic acid, in a suitable solvent such as chloroform to produce the chromeno-fused naphthopyran represented by graphic formula XXVII. Compound XXVI may be reduced with lithium aluminum hydride or reacted with a Grignard reagent in the manner described in Reaction H to derivatize the oxo group accordingly.

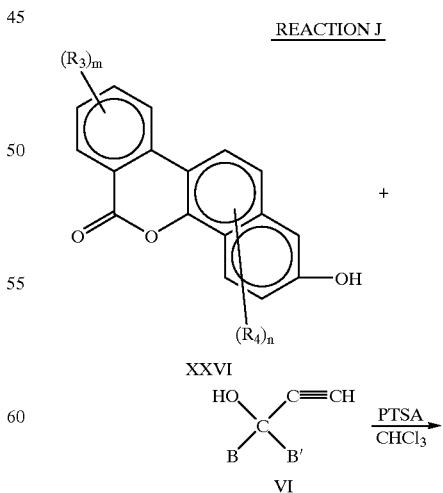

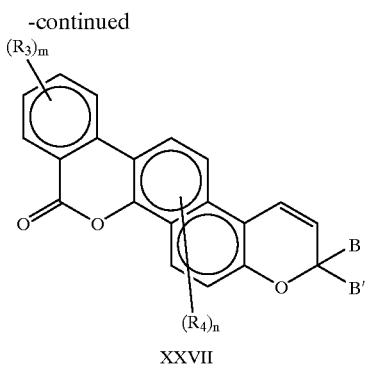

XXVII

Compounds represented by graphic formulae Ia, Ib, Ic and Id may be used in those applications in which organic photochromic substances may be employed, such as optical lenses, e.g., vision correcting ophthalmic lenses and plano lenses, face shields, goggles, visors, camera lenses, windows, automotive windshields, aircraft and automotive transparencies, e.g., T-roofs, sidelights and backlights, plastic films and sheets, textiles and coatings, e.g., coating compositions such as paints, and verification marks on security documents, e.g., documents such as banknotes, passports and drivers, licenses for which authentication or verification of authenticity may be desired. The benzopyrano-fused naphthopyrans represented by graphic formulae Ia and Ib exhibit color changes from colorless to colors ranging from yellow to blue. The chromeno-fused naphthopyrans represented by graphic formulae Ic and Id exhibit color changes from colorless to colors ranging from yellow to purple.

Examples of contemplated naphthopyran compounds within the scope of the invention include the following:

a) 2,2-bis(4-methoxyphenyl)-10-oxo-2,10-dihydro[2]benzopyrano[4',3':3,4]naphtho(2,1-b)pyran;
b) 6,6-bis(4-methoxyphenyl)-10-oxo-6,10-dihydro[2]benzopyrano[3',4':3,4]naphtho(1,2-b)pyran;
c) 6,6-bis(4-methoxyphenyl)-6,10-dihydro[2]benzopyrano[3',4':3,4]naphtho(1,2-b)pyran;
d) 2-(4-methoxyphenyl)-2-(4-morpholinophenyl)-10-oxo-2,10-dihydro[2]benzopyrano[4',3':3,4] naphtho(2,1-b)pyran;
e) 6-(4-methoxyphenyl)-6-(4-morpholinophenyl)-10-oxo-6,10-dihydro[2]benzopyrano[3',4':3,4]naphtho(1,2-b)pyran;
f) 10,10-dimethyl-6-(4-methoxyphenyl)-6-(4-morpholinophenyl)-6,10-dihydro[2]benzopyrano[3',4':3,4]naphtho(1,2-b)pyran;
g) 2-(4-morpholinophenyl)-2-phenyl-10-oxo-2,10-dihydro[2]benzopyrano[4',3':3,4]naphtho(2,1-b)pyran;
h) 6-(4-morpholinophenyl)-6-phenyl-10-oxo-6,10-dihydro[2]benzopyrano[3',4':3,4]naphtho(1,2-b)pyran;
i) 2,2-bis(4-methoxyphenyl,)-12,13-dimethoxy-10-oxo-2,10-dihydro[2]benzopyrano[4',3':3,4]naphtho(2,1-b)pyran;
j) 6,6-bis(4-methoxyphenyl)-12,13-dimethoxy-10-oxo-6,10-dihydro[2]benzopyrano [3',4':3,4]naphtho(1,2-b)pyran;
k) 6-(4-methoxyphenyl)-6-phenyl-12,13-dimethoxy-10-oxo-6,10-dihydro[2]benzopyrano[3',4':3,4]naphtho-(1,2-b)pyran;
l) 2-(4-methoxyphenyl)-2-phenyl-12,13-dimethoxy-10-oxo-2,10-dihydro[2]benzopyrano[4',3':3,4]naphtho(2,1-b)pyran;
m) 6-(4-methoxyphenyl)-6-phenyl-12,13-dimethoxy-10,10-dimethyl-6,10-dihydro[2]benzopyrano [3',4':3,4]naphtho(1,2-b)pyran;
n) 2,2-bis(4-methoxphenyl)-12-methoxy-10-oxo-2,10-dihydro[2]benzopyrano[4',3':3,4]naphtho(2,1-b)pyran;
o) 6,6-bis(4-methoxyphenyl)-12-methoxy-10-oxo-6,10-dihydro[2]benzopyrano[3',4':3,4]naphtho(1,2-b)pyran;
p) 6,6-diphenyl-9-oxo-6,9-dihydro[1]benzopyrano[3',4':3,4]naphtho(1,2-b)pyran; and
q) 3,3-diphenyl-8-oxo-3,8-dihydro[2]benzopyrano[3',4':5,6]naphtho(2,1-b)pyran.

It is contemplated that the organic photochromic naphthopyrans of the present invention may be used alone, in combination with other naphthopyrans of the present invention, or in combination with one or more other appropriate complementary organic photochromic materials, i.e., organic photochromic compounds having at least one activated absorption maxima within the range of between about 400 and 700 nanometers, or substances containing same, and may be incorporated, e.g., dissolved or dispersed, in a polymeric organic host material used to prepare photochromic articles and which color when activated to an appropriate hue.

Other than where otherwise indicated, all numbers expressing wavelengths, quantities of ingredients or reaction conditions used herein are to be understood as modified in all instances by the term "about".

Examples of complementary organic photochromic compounds include other naphthopyrans, chromenes and oxazines, substituted 2H-phenanthro[4,3-b]pyran and 3H-phenanthro[1,2-b]pyran compounds, benzopyran compounds having substituents at the 2-position of the pyran ring including a dibenzo-fused 5 member heterocyclic compound and a substituted or unsubstituted heterocyclic ring, such as a benzothieno or benzofurano ring fused to the benzene portion of the benzopyrans, spiro(benzindoline) naphthopyrans, spiro (indoline)benzopyrans, spiro (indoline) naphthopyrans, spiro(indoline)quinopyrans, spiro (indoline) pyrans, spiro(indoline)napthoxazines, spiro (indoline)pyridobenzoxazines, spiro(benzindoline) pyridobenzoxazines, spiro(benzindoline)naphthoxazines, spiro(indoline)benzoxazines, and mixtures of such photochromic compounds. Many of such photochromic compounds are described in the open literature, e.g., U.S. Pat. Nos. 3,562,172; 3,567,605; 3,578,602; 4,215,010; 4,342,668; 4,816,584; 4,818,096; 4,826,977; 4,880,667; 4,931,219; 5,066,818; 5,238,931; 5,274,132; 5,384,077; 5,405,958; 5,429,774; 5,458,814; 5,466,398; 5,514,817; 5,552,090; 5,552,091; 5,565,147; 5,573,712; 5,578,252; 5,637,262; 5,645,767; 5,656,206; 5,658,500; 5,658,501; 5,674,432 and 5,698,141. Spiro(indoline)pyrans are also described in the text, *Techniques in Chemistry*, Volume III, "Photochromism", Chapter 3, Glenn H. Brown, Editor, John Wiley and Sons, Inc., New York, 1971.

Other complementary photochromic substances contemplated are photochromic metal-dithizonates, e.g. mercury dithizonates which are described in, for example, U.S. Pat. No. 3,361,706, fulgides and fulgimides, e.g. the 3-furyl and 3-thienyl fulgides and fulgimides which are described in U.S. Pat. No. 4,931,220 at column 20, line 5 through column 21, line 38.

The disclosures relating to such photochromic compounds in the aforedescribed patents are incorporated herein, in toto, by reference. The photochromic articles of the present invention may contain one photochromic compound or a mixture of photochromic compounds, as desired.

Each of the photochromic substances described herein may be used in amounts (or in a ratio) such that an organic host material to which the photochromic compounds or mixture of compounds is applied or in which they are incorporated exhibits a desired resultant color, e.g., a substantially neutral color when activated with unfiltered sunlight, i.e., as near a neutral color as possible given the colors of the activated photochromic compounds. Neutral gray and neutral brown colors are preferred.

A neutral gray color exhibits a spectrum that has relatively equal absorption in the visible range between 400 and 700 nanometers. A neutral brown color exhibits a spectrum in which the absorption in the 400–550 nanometer range is moderately larger than in the 550–700 nanometer range. An alternative way of describing color is in terms of its chromaticity coordinates, which describe the qualities of a color in addition to its luminance factor, i.e., its chromaticity. In the CIE system, the chromaticity coordinates are obtained by taking the ratios of the tristimulus values to their sum, e.g., $x=X/(X+Y+Z)$ and $y=Y/(X+Y+Z)$. Color as described in the CIE system can be plotted on a chromaticity diagram, usually a plot of the chromaticity coordinates x and y. See pages 47–52 of *Principles of Color Technology*, by F. W. Billmeyer, Jr., and Max Saltzman, Second Edition, John Wiley and Sons, N.Y. (1981). As used herein, a near neutral color is one in which the chromaticity coordinate values of "x" and "y" for the color are within the following ranges (D65 illuminant): $x=0.260$ to $0.400$, $y=0.280$ to $0.400$ following activation to 40 percent luminous transmission by exposure to solar radiation (Air Mass 1 or 2).

The amount of photochromic substance or composition containing same applied to or incorporated into a host material is not critical provided that a sufficient amount is used to produce a photochromic effect discernible to the naked eye upon activation. Generally such amount can be described as a photochromic amount. The particular amount used depends often upon the intensity of color desired upon irradiation thereof and upon the method used to incorporate or apply the photochromic substances. Typically, the more photochromic substance applied or incorporated, the greater is the color intensity up to a certain limit.

The relative amounts of the aforesaid photochromic compounds used will vary and depend in part upon the relative intensities of the color of the activated species of such compounds, and the ultimate color desired. Generally, the amount of total photochromic substance incorporated into or applied to a photochromic optical host material may range from 0.05 to 1.0, e.g., from 0.1 to 0.45, milligrams per square centimeter of surface to which the photochromic substance(s) is incorporated or applied.

The photochromic substances of the present invention may be applied to or incorporated into a host material such as a polymeric organic host material by various methods described in the art. Such methods include dissolving or dispersing the photochromic substance within the host material, e.g., casting it in place by adding the photochromic substance to the monomeric host material prior to polymerization; imbibition of the photochromic substance into the host material by immersion of the host material in a hot solution of the photochromic substance or by thermal transfer; providing the photochromic substance as a separate layer between adjacent layers of the host material, e.g., as a part of a polymeric film; applying the photochromic substance as part of a coating or film placed on the surface of the host material; and applying a photochromic polymeric overlay section to the surface of the host material. The overlay section may have a vision correcting feature. The term "imbibition" or "imbibe" is intended to mean and include permeation of the photochromic substance alone into the host material, solvent assisted transfer of the photochromic substance into a porous polymer, vapor phase transfer, and other such transfer mechanisms.

Compatible (chemically and color-wise) tints, i.e., dyes, may be applied to the host material to achieve a more aesthetic result, for medical reasons, or for reasons of fashion. The particular dye selected will vary and depend on the aforesaid need and result to be achieved. In one embodiment, the dye may be selected to complement the color resulting from the activated photochromic substances, e.g., to achieve a more neutral color or absorb a particular wavelength of incident light. In another embodiment, the dye may be selected to provide a desired hue to the host matrix when the photochromic substances is in an unactivated state.

The host material will usually be transparent, but may be translucent or even opaque. The host material need only be transparent to that portion of the electromagnetic spectrum, which activates the photochromic substance, i.e., that wavelength of ultraviolet (UV) light that produces the open form of the substance and that portion of the visible spectrum that includes the absorption maximum wavelength of the substance in its UV activated form, i.e., the open form. Preferably, the host color should not be such that it masks the color of the activated form of the photochromic substance, i.e., so the change in color is readily apparent to the observer. More preferably, the host material article is a solid transparent or optically clear material, e.g., materials suitable for optical applications, such as plano and ophthalmic lenses, windows, automotive transparencies, e.g., windshields, aircraft transparencies, plastic sheeting, polymeric films, etc.

The photochromic compounds of the present invention may be present in an organic solvent or an organic polymeric host. The organic solvent may be selected from the group consisting of benzene, toluene, methyl ethyl ketone, acetone, ethanol, tetrahydrofurfuryl alcohol, N-methyl pyrrolidinone, 2-methoxyethyl ether, xylene, cyclohexane, 3-methyl cyclohexanone, ethyl acetate, tetrahydrofuran, methanol, methyl propinate, ethylene glycol and mixtures thereof. Preferably, the organic solvent is selected from the group consisting of acetone, ethanol, tetrahydrofurfuryl alcohol, 2-methoxyethyl ether, 3-methyl cyclohexanone, N-methyl pyrrolidinone and mixtures thereof.

Preferably, the organic polymeric host material is a solid transparent or optically clear material, e.g., materials suitable for optical applications, such as plano and ophthalmic lenses, windows, automotive transparencies, e.g., windshields, aircraft transparencies, plastic sheeting, polymeric films, etc.

Examples of polymeric organic host materials are polymers prepared from individual monomers or mixtures of monomers selected from the following groups:

(a) diacrylate or dimethacrylate compounds represented by graphic formula XXVIII:

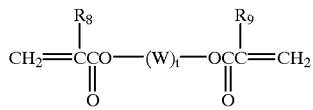

XXVIII wherein $R_8$ and $R_9$ may be the same or different and are hydrogen or methyl, W is $(CH_2)$, and t is an integer of from 1 to 20;

(b) diacrylate or dimethacrylate compounds represented by graphic formula XXIX:

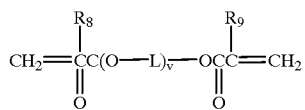

XXIX wherein L is a straight or branched chain alkylene containing from 2 to 4 carbon atoms, and v is an integer of from 1 to 50; and (c) an acrylate or a methacrylate compound having an epoxy group represented by graphic formula XXX:

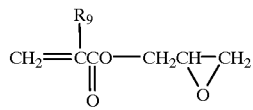

XXX

In graphic formulae XXVIII, XXIX and XXX, like letters used with respect to the definitions of different substituents have the same meaning.

Examples of diacrylate or dimethacrylate compounds, i.e., di(meth)acrylates, represented by graphic formula XXVIII include butanediol di(meth)acrylate, hexanediol di(meth)acrylate and nonanediol di(meth)acrylate, and represented by graphic formula XXIX include diethylene glycol dimethacrylate, triethylene glycol dimethacrylate and poly (oxyalkylene dimethacrylates), e.g., polyethylene glycol (600) dimethacrylate. Examples of acrylate or methacrylate compounds represented by graphic formula XXX include glycidyl acrylate and glycidyl methacrylate.

Further examples of polymeric organic host materials which may be used with the photochromic compounds described herein include: polymers, i.e., homopolymers and copolymers, of the monomers and mixtures of monomers represented by graphic formulae XXVIII, XXIX and XXX, bis(allyl carbonate) monomers, diisopropenyl benzene monomers, ethoxylated bisphenol A dimethacrylate monomers, ethylene glycol bismethacrylate monomers, poly (ethylene glycol) bis-methacrylate monomers, ethoxylated phenol bismethacrylate monomers, alkoxylated polyhydric alcohol polyacrylate monomers, such as ethoxylated trimethylol propane triacrylate monomers, urethane acrylate monomers, such as those described in U.S. Pat. No. 5,373,033, and vinylbenzene monomers, such as those described in U.S. Pat. No. 5,475,074 and styrene; polymers, i.e., homopolymers and copolymers, of polyfunctional, e.g., mono-, di- or multi-functional, acrylate and/or methacrylate monomers, poly($C_1$–$C_{12}$ alkyl methacrylates), such as poly (methyl methacrylate), poly(alkoxylated phenol methacrylates), cellulose acetate, cellulose triacetate, cellulose acetate propionate, cellulose acetate butyrate, poly (vinyl acetate), poly(vinyl alcohol), poly(vinyl chloride), poly(vinylidene chloride), polyurethanes, thermoplastic polycarbonates, polyesters, poly(ethylene terephthalate), polystyrene, poly(alpha methylstyrene), copoly(styrene-methyl methacrylate), copoly(styrene-acrylonitrile), polyvinylbutyral and polymers, i.e., homopolymers and copolymers, of diallylidene pentaerythritol, particularly copolymers with polyol (allyl carbonate) monomers, e.g., diethylene glycol bis(allyl carbonate), and acrylate monomers, e.g., ethyl acrylate, butyl acrylate.

Transparent copolymers and blends of transparent polymers are also suitable as host materials. Preferably, the host material is an optically clear polymerized organic material prepared from a thermoplastic polycarbonate resin, such as the carbonate-linked resin derived from bisphenol A and phosgene, which is sold under the trademark, LEXAN; a polyester, such as the material sold under the trademark, MYLAR; a poly(methyl methacrylate), such as the material sold under the trademark, PLEXIGLAS; polymerizates of a polyol(allyl carbonate) monomer, especially diethylene glycol bis(allyl carbonate), which monomer is sold under the trademark CR-39, and polymerizates of copolymers of a polyol (allyl carbonate), e.g., diethylene glycol bis(allyl carbonate), with other copolymerizable monomeric materials, such as copolymers with vinyl acetate, e.g., copolymers of from 80–90 percent diethylene glycol bis (allyl carbonate) and 10–20 percent vinyl acetate, particularly 80–85 percent of the bis(allyl carbonate) and 15-20 percent vinyl acetate, and copolymers with a polyurethane having terminal diacrylate functionality, as described in U.S. Pat. Nos. 4,360,653 and 4,994,208; and copolymers with aliphatic urethanes, the terminal portion of which contain allyl or acrylyl functional groups, as described in U.S. Pat. No. 5,200,483; poly(vinyl acetate), polyvinylbutyral, polyurethane, polymers of members of the group consisting of diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers and ethoxylated trimethylol propane triacrylate monomers; cellulose acetate, cellulose propionate, cellulose butyrate, cellulose acetate butyrate, polystyrene and copolymers of styrene with methyl methacrylate, vinyl acetate and acrylonitrile.

More particularly, contemplated is use of the photochromic naphthopyrans of the present invention with optical organic resin monomers used to produce optically clear polymerizates, i.e., materials suitable for optical applications, such as for example plano and ophthalmic lenses, windows, and automotive transparencies. Such optically clear polymerizates may have a refractive index that may range from about 1.48 to about 1.75, e.g., from about 1.495 to about 1.66. Specifically contemplated are optical resins sold by PPG Industries, Inc. under the CR-designation, e.g., CR-307 and CR-407.

The present invention is more particularly described in the following examples which are intended as illustrative only, since numerous modifications and variations therein will be apparent to those skilled in the art.

EXAMPLE 1

Step 1

1,3-Dihydroxynaphthalene (5 grams), o-bromobenzoic acid (5 grams) and sodium hydroxide (2 grams) were mixed into a reaction flask containing 50 milliliters (mL) water. The mixture was refluxed for two minutes. A 20 weight percent copper sulfate solution (2 mL) was added dropwise to the reaction mixture followed by refluxing for five minutes. The mixture was filtered to obtain 3.5 grams of a solid which was determined via nuclear magnetic resonance (NMR) spectra to include two products having structures consistent with 11-hydroxy-6-oxo-6H-dibenzo[c,h][1]benzopyran and 8-hydroxy-5-oxo-5H-dibenzo[c,f][1]benzopyran.

Step 2

The product from Step 1 (3.5 grams) and 1,1-bis(4-methoxyphenyl)-2-propyn-1-ol (2.1 grams) were added to a reaction flask containing chloroform (100 mL) and stirred at room temperature. p-Toluene sulfonic acid (0.1 gram) was added to the reaction mixture and stirred for three hours. The solvent was evaporated leaving an oily residue which crystallized in acetone:diethylether mixture (1:2). The product was separated via filtration to obtain a filtrate and the crystals. The crystals were washed and dried yielding 0.4 gram of a first product having a melting point of 267–269° C. The filtrate was concentrated and purified via column chromatography using chloroform as the eluant and yielded 0.9 gram of a second product having a melting point of 185–186° C. NMR spectra showed the first product (Compound 1A) to have a structure consistent with 2,2-bis(4-methoxyphenyl)-10-oxo-2,10-dihydro[2]benzopyrano[4',3':3,4]naphtho(2,1-b)pyran, and the second product (Compound 1B) to have a structure consistent with 6,6-bis(4-methoxyphenyl)-10-oxo-6,10-dihydro[2]benzopyrano[3',4':3,4]naphtho(1,2-b)pyran.

EXAMPLE 2

6,6-Bis(4-methoxyphenyl)-10-oxo-6,10-dihydro[2]benzopyrano[3'4':3,4]naphtho(1,2-b)pyran (1.0 gram) produced according to the process described in Example 1 was mixed into a reaction flask containing anhydrous tetrahydrofuran (THF) (50 mL) and stirred at room temperature. Lithium aluminum hydride (0.05 gram) was slowly added to the mixture and stirred for three hours. The reaction mixture was poured into a beaker containing ice and a five weight percent solution of hydrochloric acid and stirred for one hour. The organic layer was separated, washed with water, dried and concentrated. The concentrate was purified via column chromatography using a chloroform:hexane (1:1) eluant to yield 0.3 gram of a product having a melting point of 228–230° C. An NMR spectrum showed the product (Compound 2) to have a structure consistent with 6,6-bis(4-methoxyphenyl)-6,10-dihydro[2]benzopyrano[3'4':3,4]naphtho(1,2-b)pyran.

EXAMPLE 3

A naphthol mixture (2.0 gram) produced according to the process described in Example 1, Step 1 and 1-(4-methoxyphenyl)-4-morpholinophenyl-2-propyn-1-ol were added to a reaction flask containing chloroform (50 mL) and stirred at room temperature. p-Toluene sulfonic acid (0.1 gram) was added to the reaction mixture and stirred for 8 hours. The solvent (chloroform) was evaporated and the residue was dissolved in acetone. After one day, a solid crystallized out from the solution. The product mixture was separated via filtration to produce a filtrate and a solid. The solid was washed with acetone and air dried to yield 0.9 gram of a first product having a melting point of 226–228° C. The filtrate was concentrated and purified via column chromatography to yield 0.55 gram of a second product having a melting point of 200–204° C. NMR spectra showed the first product (Compound 3A) to have a structure consistent with 2-(4-methoxyphenyl)-2-(4-morpholinophenyl)-10-oxo-2,10-dihydro[2]benzopyrano[4',3':3,4]naphtho(2,1-b)pyran and the second product (Compound 3B) to have a structure consistent with 6-(4-methoxyphenyl)-6-(4-morpholinophenyl)-10-oxo-6,10-dihydro[2]benzopyrano[3',4':3,4]naphtho(1,2-b)pyran.

EXAMPLE 4

6-(4-methoxyphenyl)-6-(4-morpholinophenyl)-10-oxo-6,10-dihydro[2]benzopyrano[3',4':3,4]naphtho(1,2-b)pyran (0.5 gram) from Example 3 was mixed into a reaction flask containing anhydrous THF (50 mL) and stirred at room temperature. Methyl magnesium chloride in threefold stoichiometric excess was added slowly to the mixture and stirred for two hours. The reaction mixture was poured into a 250 mL beaker containing ice and hydrochloric acid (50 mL) and stirred for three hours. The organic layer was separated, washed with water and dried over sodium sulfate. The solvent (THF) was evaporated to produce an oily residue which was purified via column chromatography to yield 0.1 gram of a non-crystalline product. An NMR spectrum showed the product (Compound 4) to have a structure consistent with 10,10 -dimethyl-6-(4-methoxyphenyl)-6-(4-morpholinophenyl)-6,10-dihydro[2]benzopyrano[3',4':3,4]naphtho(1,2-b)pyran.

EXAMPLE 5

A mixture of 11-hydroxy-6-oxo-6H-benzo[c,h][1]dibenzopyran and 8-hydroxy-5-oxo-5H-dibenzo[c,f][1]benzopyran produced according to Example 1, Step 1 and 1-phenyl-1-(4-morpholinophenyl)-2-propyn-1-ol (3.5 grams) were added to a reaction flask containing chloroform (150 mL) and stirred at room temperature. p-Toluene sulfonic acid (0.1 gram) was added to the reaction mixture and stirred for 12 hours. The solvent (chloroform) was evaporated leaving an oily residue which crystallized from acetone. The product mixture was separated to produce a filtrate and crystals. The crystals were washed with acetone and air dried to yield 0.6 gram of a first product having a melting point of 228–230° C. The filtrate was concentrated and purified via column chromatography to yield 0.8 gram of a second product having a melting point of 162–164° C. NMR spectra showed the first product (Compound 5A) to have a structure consistent with 2-(4-morpholinophenyl)-2-phenyl-10-oxo-2,10-dihydro[2]benzopyrano[4',3':3,4]naphtho(2,1-b)pyran and the second product (Compound 5B) to have a structure consistent with 6-(4-morpholinophenyl)-6-phenyl-10-oxo-6,10-dihydro[2]benzopyrano[3',4':3,4]naphtho(1,2-b)pyran.

EXAMPLE 6

The process of Example 1 was followed except that in Step 1, 4,5-dimethoxy-2-bromobenzoic acid was used in place of o-bromobenzoic acid, 40 mL of water were used, a 10 weight percent solution of copper sulfate was used in place of 20 percent copper sulfate solution and the reaction mixture was refluxed for 20 minutes. The reaction mixture was cooled and filtered to obtain 3.5 grams of a naphthol mixture. In Step 2, 50 mL of chloroform was used. Evaporation of the solvent resulted in a product mixture which was filtered to produce a solid and a filtrate. The solid was washed and dried yielding 0.4 grams of a first product having a melting point of 230–231° C. The filtrate was concentrated and purified via column chromatography to yield 0.5 gram of a second product having a melting point of 135–136° C. NMR spectra showed the first product (Compound 6A) to have a structure consistent with 2,2-bis(4-methoxyphenyl)-12,13-dimethoxy-10-oxo-2,10-dihydro[2]benzopyrano[4',3':3,4]naphtho(2,1-b)pyran and the second product (Compound 6B) to have a structure consistent with 6,6-bis(4-methoxyphenyl)-12,13-dimethoxy-10-oxo-6,10-dihydro[2]benzopyrano[3',4':3,4]naphtho(1,2-b)pyran.

EXAMPLE 7

The process of Example 6 was followed except that in Step 2, 1.5 grams of the naphthol mixture was used, 1.5 grams of 1-phenyl-1-(4-methoxyphenyl)-2-propyn-1-ol was used in place of 2.1 grams of 1,1-di(4-methoxyphenyl)-2-propyn-1-ol, 50 mL of chloroform was used and the reaction mixture was stirred for 4 hours. The solvent (chloroform) was evaporated and the residue was purified via column chromatography using chloroform:hexane (1:1) as eluant. One fraction of a first product (0.4 gram) having a melting point of 198–200° C. and another fraction of a second product (0.3 gram) having a melting point of 194–195° C. were obtained. NMR spectra showed the first product (Compound 7A) to have a structure consistent with 6-(4-methoxyphenyl)-6-phenyl-12,13-dimethoxy-10-oxo-6,10-dihydro[2]benzopyrano[3',4':3,4]naphtho(1,2-b)pyran and the second product (Compound 7B) to have a structure consistent with 2-(4-methoxphenyl)-2-phenyl-12,13-dimethoxy-10-oxo-2,10-dihydro[2]benzopyrano[4',3':3,4]naphtho(2,1-b)pyran.

EXAMPLE 8

6-(4-Methoxyphenyl)-6-phenyl-12,13-dimethoxy-10-oxo-6,10-dihydro[2]benzopyrano[3',4':3,4]naphtho(1,2-b)pyran (0.5 gram) produced in Example 7 was mixed into a reaction flask containing THF (25 mL) and stirred at room temperature. Methyl magnesium bromide in threefold stoichiometric excess was added slowly to the mixture and stirred for three hours. The reaction mixture was poured into a beaker containing ice and hydrochloric acid (5 weight percent solution, 50 mL) and stirred for one half hour. The organic layer was separated, washed with water, dried and concentrated. The concentrate was purified via column chromatography using a chloroform:hexane mixture (1:1) as the eluant to yield 0.2 gram of the desired product. An NMR spectrum showed the product (Compound 8) to have a structure consistent with 6-(4-methoxyphenyl)-6-phenyl-12,13-dimethoxy-10,10-dimethyl-6,10-dihydro[2]benzopyrano[3',4':3,4]naphtho(1,2-b)pyran.

EXAMPLE 9

Step 1

1,3-Dihydroxynaphthalene (2 grams), 5-methoxy-2-bromobenzoic acid (2.5 grams) and sodium hydroxide (1 gram) were mixed into a reaction flask containing water (30 mL) and refluxed for one minute. Copper sulfate solution (10 weight percent, 1 mL) was added dropwise to the reaction mixture and refluxed for 30 minutes. The reaction mixture was cooled and a solid precipitate formed. The solid was filtered, washed and dried yielding 1.3 grams of a product used directly in the next step.

Step 2

The product (1.0 gram) from Step 1 and 1,1-di(4-methoxyphenyl)-2-propyn-1-ol (1.0 gram) were added to a reaction flask containing chloroform (30 mL) and stirred. p-Toluene sulfonic acid (0.1 gram) was added to the reaction mixture and stirred for six hours. The solvent (chloroform) was evaporated and the residue was column purified using a chloroform-hexane mixture (1:1) as the eluant. One fraction of a first product (0.2 gram) having a melting point of 235–237° C. and another fraction of a second product (0.3 gram) were obtained. NMR spectra showed the first product (Compound 9A) to have a structure consistent with 2,2-bis(4-methoxyphenyl)-12-methoxy-10-oxo-2,10-dihydro[2]benzopyrano[4',3':3,4]naphtho(2,1-b)pyran and the second product (Compound 9B) to have a structure consistent with 6,6-bis(4-methoxyphenyl)-12-methoxy-10-oxo-6,10-dihydro[2]benzopyrano[3',4':3,4]naphtho(1,2-b)pyran

EXAMPLE 10

Step 1

Ortho-bromophenol (10 grams) and 3,4-dihydro-2H-pyran (10 grams) were mixed into a reaction flask containing methylene chloride (100 mL). Pyridinium p-toluene sulfonate (1 gram) was added to the reaction mixture and stirred for four hours. Cold water (100 mL) was added to the reaction mixture and stirred for one half hour. The organic layer was separated, washed with a sodium hydroxide (5 percent solution), washed with water, and dried over magnesium sulfate. The solvent was evaporated yielding 14 grams of an oily product. An NMR spectrum showed the product to have a structure consistent with 2-(2-bromophenyloxy)perhydropyran.

Step 2

2-(2-Bromophenyloxy)perhydropyran (10 grams) from Step 1 and magnesium turnings were mixed into a reaction flask containing THF (100 mL). A catalytic amount of dibromoethane was added to the reaction mixture. Upon dissolution of the magnesium, 2,2-diphenyl-5-carbomethoxy-6-methoxy-2H-naphtho[1,2-b]pyran (2 grams) dissolved in THF (20 mL) was added to the reaction mixture and stirred for 8 hours. The mixture was added to a mixture of hydrochloric acid (10 percent) and ice and was stirred for one half hour. The organic layer was separated, washed, dried and concentrated. The concentrate was column purified yielding 1 gram of a first product and 0.1 gram of a second product having a melting point of 194-196OC. NMR spectra and mass spectrographs showed the first product to have a structure consistent with 2,2-diphenyl-5-carbomethoxy-6-(2-hydroxyphenyl)-2H-naphtho[2,1-b]pyran and the second product (Compound 10) to have a structure consistent with 6,6-diphenyl-9-oxo-6,9-dihydro[1]benzopyrano[3',4':3,4]naphtho(1,2-b)pyran.

EXAMPLE 11

Step 1

1,6-Dihydroxynaphthalene (5.0 grams), 2-bromobenzoic acid (5.0 grams) and sodium hydroxide (2.0 grams) were mixed into a reaction flask containing water (50 mL) and refluxed for two minutes. Aqueous copper sulfate solution (10 percent, 2 mL) was added slowly to the reaction mixture and refluxed for 20 minutes. The mixture was cooled to room temperature producing a solid precipitate. The solid was filtered, washed with water several times and oven dried yielding 1 gram of a product. An NMR spectrum showed the product to have a structure consistent with 2-hydroxy-6-oxo-6H-dibenzo[c,h][1]benzopyran.

Step 2

2-Hydroxy-6-oxo-6H-dibenzo[c,h][1]benzopyran (0.5 gram) from Step 1 and 2,2-diphenyl-2-propyn-1-ol (1 gram) were mixed into a reaction flask containing chloroform (100 mL) and stirred at room temperature. p-Toluene sulfonic acid (0.1 gram) was added to the reaction mixture and stirred for two days. The mixture was filtered to remove unreacted naphthol. The filtrate was concentrated, and a solid was crystallized from diethyl ether. The solid was filtered, washed with a small amount of ether and air dried yielding 0.1 gram of a product having a melting point of 274–276° C. An NMR spectrum showed the product (Compound 11) to have a structure consistent with 3,3-diphenyl-8-oxo-3,8-dihydro[2]benzopyrano[3',4':5,6]naphtho(2,1-b)pyran.

EXAMPLE 12

PART A

Testing was done with the photochromic compounds prepared in Examples 1–11 in the following manner. A quantity of each photochromic compound calculated to yield a $1.5 \times 10^{-3}$ molal solution was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis(2-methyl propionitrile) (AIBN). Each photochromic compound was dissolved into the monomer blend by stirring and gentle heating. After a clear solution was obtained, it was poured into a flat sheet mold having the interior dimensions of 2.2 mm×6 inches (15.24 cm)×6 inches (15.24 cm).

The mold was sealed and placed in a horizontal air flow, programmable oven programmed to increase the temperature from 40° C. to 95° C. over a hour interval, hold the temperature at 95° C. for 3 hours, lower it to 60° C. over a 2 hour interval and then hold at 60° C. for 16 hours. After the mold was opened, the polymer sheet was cut using a diamond blade saw into 2 inch (5.1 centimeters) test squares.

Part B

The photochromic test squares prepared in Part A were tested for photochromic response on an optical bench. Prior to testing on the optical bench, the photochromic test squares were exposed to 365 nanometer ultraviolet light for about 15 minutes to activate the photochromic compounds and then placed in a 76° C. oven for about 15 minutes to bleach or inactivate the photochromic compounds. The test squares were then cooled to room temperature, exposed to fluorescent room lighting for at least 2 hours and then kept covered for at least 2 hours prior to testing on an optical bench maintained at 72° F. (22.2° C.). The bench was fitted with a 150 watt Xenon arc lamp, a remote controlled shutter, a copper sulfate bath acting as a heat sink for the arc lamp, a Schott WG-320 nm cut-off filter which removes short wavelength radiation; neutral density filter(s) and a sample holder in which the square to be tested was inserted. The power output of the optical bench, i.e., the dosage of light that the sample lens would be exposed to, was calibrated with a photochromic test square used as a reference standard. This resulted in a power output ranging from 0.15 to 0.20 milliWatts per square centimeter ($mW/cm^2$). Measurement of the power output was made using a GRASEBY Optronics Model S-371 portable photometer (Serial #21536) with a UV-A detector (Serial #22411) or comparable equipment. The UV-A detector was placed into the sample holder and the light output was measured. Adjustments to the power output were made by increasing or decreasing the lamp wattage or by adding or removing neutral density filters in the light path.

A monitoring, collimated beam of light from a tungsten lamp was passed through the square at a small angle (approximately 300) normal to the square. After passing through the square, the light from the tungsten lamp was directed to a detector through Spectral Energy Corp. GM-200 monochromator set at the previously determined visible lambda max of the photochromic compound being measured. The output signals from the detector were processed by a radiometer.

Change in optical density (ΔOD) was determined by inserting a test square in the bleached state into the sample holder, adjusting the transmittance scale to 100%, opening the shutter from the Xenon lamp to provide ultraviolet radiation to change the test square from the bleached state to an activated (i.e., darkened) state, measuring the transmittance in the activated state, and calculating the change in optical density according to the formula: ΔOD=log(100/% Ta), where % Ta is the percent transmittance in the activated state and the logarithm is to the base 10.

The optical properties of the photochromic compound in the test squares are reported in Table 1. The Δ OD/min, which represents the sensitivity of the photochromic compound's response to UV light, was measured over the first five (5) seconds of UV exposure, then expressed on a per minute basis. The saturation optical density (Δ OD@ Saturation) was taken under identical conditions as the Δ OD/min, except UV exposure was continued for 15 minutes. The lambda max (Vis) is the wavelength in nanometers (nm) in the visible spectrum at which the maximum absorption of the activated (colored) form of the photochromic compound in a test square occurs. The lambda max (Vis) wavelength was determined by testing the photochromic test square polymerizates of Part A in a Varian Cary 3 UV-Visible spectrophotometer. The Bleach Rate (T ½) is the time interval in seconds for the absorbance of the activated form of the photochromic compound in the test squares to reach one half the highest absorbance at room temperature (72° F., 22.20C.) after removal of the source of activating light.

TABLE 1

| Compound Example | lambda max (Vis) nanometers | Sensitivity ΔOD/min | ΔOD @ Saturation | Bleach Rate T 1/2 (sec) |
|---|---|---|---|---|
| 1A | 493 | 0.29 | 0.14 | 18 |
| 1B | 537 | 0.19 | 0.07 | 24 |
| 2A | 546 | 0.10 | 0.22 | 116 |
| 2B | 432 | 0.12 | 0.27 | 112 |
| 3A | 530 | 0.04 | 0.01 | 3 |
| 3B | 598 | 0.13 | 0.06 | 39 |
| 4A | 598 | 0.18 | 0.23 | 68 |
| 4B | 472 | 0.12 | 0.19 | 61 |
| 5A | 570 | 0.21 | 0.12 | 37 |
| 6A | 477 | 0.19 | 0.13 | 28 |
| 6B | 569 | 0.22 | 0.10 | 32 |
| 7A | 569 | 0.27 | 0.22 | 54 |
| 7B | 464 | 0.31 | 0.29 | 47 |
| 8 | 602 | 0.08 | 0.21 | 216 |
| 9A | 478 | 0.25 | 0.12 | 24 |
| 10 | 484 | 0.69 | 0.26 | 19 |
| 11 | 466 | 0.12 | 0.02 | 22 |

The results of Table 1 show that test squares prepared using the Compounds of Examples 1 through 11 demonstrate a wide range of colors, from yellow at 432 nm to blue at 602 nm, coloration rates (sensitivity) from 0.04 to 0.69, activated intensity (ΔOD at Saturation) from 0.01 to 0.29, and fade or bleach rates from 3 to 216 seconds.

The present invention has been described with reference to specific details of particular embodiments thereof. It is not intended that such details be regarded as limitations upon the scope of the invention except insofar as to the extent that they are included in the accompanying claims.

We claim:

1. A naphthopyran compound represented by the following graphic formulae:

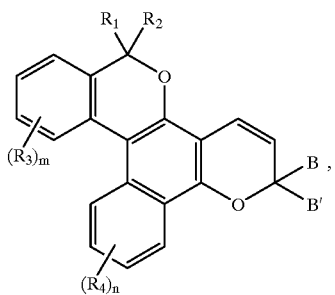

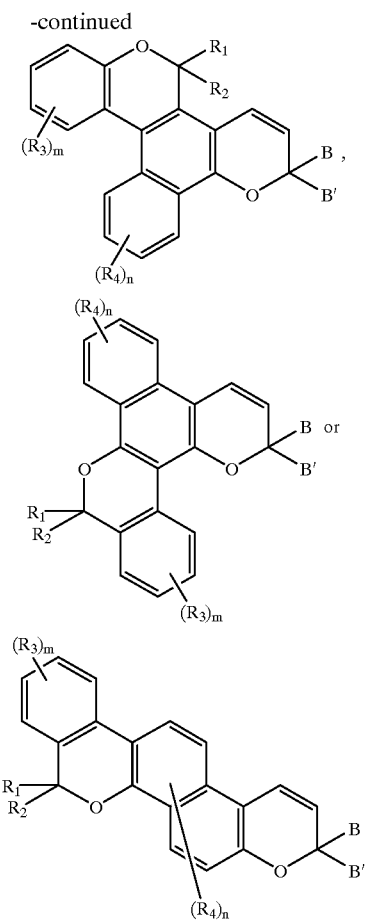

wherein, (a) $R_1$ and $R_2$ together form an oxo group or $R_1$ and $R_2$ are each hydrogen, $C_1$–$C_6$ alkyl, $C_3$–$C_7$ cycloalkyl, allyl, phenyl, mono- or di-substituted phenyl, benzyl or mono-substituted benzyl, each of said phenyl and benzyl group substituents being $C_1$–$C_6$ alkyl or $C_1$–$C_6$ alkoxy;

(b) each $R_3$ and $R_4$ are selected from the group consisting of $C_1$–$C_6$ alkyl, $C_1$–$C_6$ alkoxy, chloro and fluoro, and m and n are each the integer 0, 1 or 2; and (c) B and B' are each selected from the group consisting of:
  (i) the unsubstituted, mono-, di- and tri-substituted aryl groups, phenyl and naphthyl;
  (ii) the unsubstituted, mono- and di-substituted heteroaromatic groups pyridyl, furanyl, benzofuran-2-yl, benzofuran-3-yl, thienyl, benzothien-2-yl, benzothien-3-yl, each of said aryl and heteroaromatic substituents in parts (i) and (ii) being selected from the group consisting of phenyl, phenyl($C_1$–$C_3$) alkyl, di($C_1$–$C_6$)alkylamino, piperidino, morpholino, pyrryl, $C_1$–$C_6$ alkyl, $C_1$–$C_6$ chloroalkyl, $C_1$–$C_6$ fluoroalkyl, $C_1$–$C_6$ alkoxy, mono($C_1$–$C_6$)alkoxy ($C_1$–$C_4$)alkyl, acryloxy, methacryloxy, chloro and fluoro;
  (iii) the groups represented by the following graphic formulae:

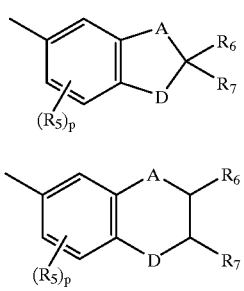

wherein A may be carbon or oxygen and D may be oxygen or substituted nitrogen, provided that when D is substituted nitrogen, A is carbon, said nitrogen substituents being selected from the group consisting of hydrogen, $C_1-C_6$ alkyl and $C_2-C_6$ acyl; each $R_5$ is $C_1-C_6$ alkyl, $C_1-C_6$ alkoxy, hydroxy, chloro or fluoro; $R_6$ and $R_7$ are each hydrogen or $C_1-C_6$ alkyl; and p is the integer 0, 1 or 2;

(iv) $C_1-C_6$ alkyl, $C_1-C_6$ chloroalkyl, $C_1-C_6$ fluoroalkyl, $C_1-C_6$ alkoxy($C_1-C_4$)alkyl, $C_3-C_6$ cycloalkyl, mono($C_1-C_6$)alkoxy($C_3-C_6$)cycloalkyl, mono($C_1-C_6$)alkyl($C_3-C_6$)cycloalkyl, chloro ($C_3-C_6$)cycloalkyl and fluoro($C_3-C_6$)cycloalkyl; and (v) the group represented by the following graphic formula:

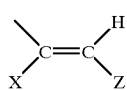

wherein X may be hydrogen or $C_1-C_4$ alkyl and Z may be selected from the unsubstituted, mono-, and di-substituted members of the group consisting of naphthyl, phenyl, furanyl and thienyl, each of said group substituents in this part (v) being $C_1-C_4$ alkyl, $C_1-C_4$ alkoxy, fluoro or chloro; or (vi) B and B' taken together form fluoren-9-ylidene, mono-, or di-substituted fluoren-9-ylidene or form a member selected from the group consisting of saturated $C_3-C_{12}$ spiro-monocyclic hydrocarbon rings, saturated $C_7-C_{12}$ spirobicyclic hydrocarbon rings, and saturated $C_7-C_{12}$ spiro-tricyclic hydrocarbon rings, each of said fluoren-9-ylidene substituents being selected from the group consisting of $C_1-C_4$ alkyl, $C_1-C_4$ alkoxy, fluoro and chloro.

2. The naphthopyran of claim 1 wherein, (a) $R_1$ and $R_2$ are each hydrogen, $C_1-C_4$ alkyl, $C_3-C_6$ cycloalkyl, phenyl, mono- or di-substituted phenyl, benzyl or mono-substituted benzyl, each of said phenyl and benzyl group substituents being $C_1-C_4$ alkyl or $C_1-C_4$ alkoxy;

(b) each $R_3$ and $R_4$ are selected from the group consisting of $C_1-C_4$ alkyl, $C_1-C_4$ alkoxy and fluoro, and m and n are each the integer 0, 1, or 2; and (c) B and B' are each selected from the group consisting of:

(i) phenyl, mono-substituted phenyl and di-substituted phenyl;

(ii) the unsubstituted, mono- and di-substituted heteroaromatic groups furanyl, benzofuran-2-yl, thienyl and benzothien-2-yl, each of said phenyl and heteroaromatic substituents being selected from the group consisting of di($C_1-C_3$)alkylamino, piperidino, morpholino, pyrryl, $C_1-C_3$ alkyl, $C_1-C_3$ chloroalkyl, $C_1-C_3$ fluoroalkyl, $C_1-C_3$ alkoxy, mono($C_1-C_3$)alkoxy($C_1-C_3$)alkyl, fluoro and chloro;

(iii) the groups represented by the graphic formulae IIA and IIB, wherein A is carbon and D is oxygen, $R_5$ is $C_1-C_3$ alkyl or $C_1-C_3$ alkoxy, $R_6$ and $R_7$ are each hydrogen or $C_1-C_4$ alkyl, and p is the integer 0 or 1;

(iv) $C_1-C_4$ alkyl; and (v) the group represented by the graphic formula IIC wherein X is hydrogen or methyl and Z is phenyl or mono-substituted phenyl, said phenyl substituent being selected from the group consisting of $C_1-C_3$ alkyl, $C_1-C_3$ alkoxy and fluoro; or (vi) B and B' taken together form fluoren-9-ylidene, mono-substituted fluoren-9-ylidene or a member selected from the group consisting of saturated $C_3-C_8$ spiro-monocyclic hydrocarbon rings, saturated $C_7-C_{10}$ spiro-bicyclic hydrocarbon rings, and saturated $C_7-C_{10}$ spiro-tricyclic hydrocarbon rings, said fluoren-9-ylidene substituent being selected from the group consisting of $C_1-C_3$ alkyl, $C_1-C_3$ alkoxy, fluoro and chloro.

3. The naphthopyran of claim 2 wherein, (a) $R_1$ and $R_2$ are each hydrogen, $C_1-C_3$ alkyl, $C_3-C_5$ cycloalkyl, phenyl, mono- or di-substituted phenyl, benzyl or mono-substituted benzyl, each of said phenyl and benzyl group substituents being $C_1-C_3$ alkyl or $C_1-C_3$ alkoxy;

(b) $R_3$ and $R_4$ are selected from the group consisting of $C_1-C_3$ alkyl and $C_1-C_3$ alkoxy, and m and n are each the integer 0, 1, or 2; and (c) B and B' are each selected from the group consisting of:

(i) phenyl, mono- and di-substituted phenyl;

(ii) the unsubstituted, mono- and di-substituted heteroaromatic groups furanyl, benzofuran-2-yl, thienyl and benzothien-2-yl, each of said phenyl and heteroaromatic substituents being selected from the group consisting of $C_1-C_3$ alkyl, $C_1-C_3$ alkoxy and fluoro; and (iii) the group represented by graphic formula IIA, wherein A is carbon and D is oxygen, $R_5$ is $C_1-C_3$ alkyl or $C_1-C_3$ alkoxy, $R_6$ and $R_7$ are each hydrogen or $C_1-C_3$ alkyl, and p is the integer 0 or 1; or (iv) B and B' taken together form fluoren-9-ylidene, adamantylidene, bornylidene, norbornylidene, or bicyclo[3.3.1]nonan-9-ylidene.

4. A naphthopyran compound selected from the group consisting of:

a) 2,2-bis(4-methoxyphenyl)-10-oxo-2,10-dihydro[2]benzopyrano[4',3':3,4]naphtho(2,1-b)pyran;

b) 6,6-bis(4-methoxyphenyl)-10-oxo-6,10-dihydro[2]benzopyrano[3',4':3,4]naphtho(1,2-b)pyran;

c) 6,6-bis(4-methoxyphenyl)-6,10-dihydro[2]benzopyrano[3',4':3,4]naphtho(1,2-b)pyran;

d) 2-(4-methoxyphenyl)-2-(4-morpholinophenyl)-10-oxo-2,10-dihydro[2]benzopyrano[4',3':3,4] naphtho(2,1-b)pyran;

e) 6-(4-methoxyphenyl)-6-(4-morpholinophenyl)-10-oxo-6,10-dihydro[2]benzopyrano[3',4':3,4]naphtho(1,2-b)pyran;

f) 10,10-dimethyl-6-(4-methoxyphenyl)-6-(4-morpholinophenyl)-6,10-dihydro[2]benzopyrano[3',4':3,4]naphtho(1,2-b)pyran;

g) 2-(4-morpholinophenyl)-2-phenyl-10-oxo-2,10-dihydro[2]benzopyrano[4',3':3,4]naphtho(2,1-b)pyran;

h) 6-(4-morpholinophenyl)-6-phenyl-10-oxo-6,10-dihydro[2]benzopyrano[3',4':3,4]naphtho(1,2-b)pyran;

i) 2,2-bis(4-methoxyphenyl)-12,13-dimethoxy-10-oxo-2,10-dihydro[2]benzopyrano[4',3':3,4]naphtho(2,1-b)pyran;

j) 6,6-bis(4-methoxyphenyl)-12,13-dimethoxy-10-oxo-6,10-dihydro[2]benzopyrano [3',4':3,4]naphtho(1,2-b)pyran;

k) 6-(4-methoxyphenyl)-6-phenyl-12,13-dimethoxy-10-oxo-6,10-dihydro[2]benzopyrano[3',4':3,4]naphtho(1,2-b)pyran;

l) 2-(4-methoxyphenyl)-2-phenyl-12,13-dimethoxy-10-oxo-2,10-dihydro[2]benzopyrano[4',3':3,4]naphtho(2,1-b)pyran;

m) 6,6-(4-methoxyphenyl)-6-phenyl-12,13-dimethoxy-10,10-dimethyl-6,10-dihydro[2]benzopyrano[3',4':3,4]naphtho(1,2-b)pyran;

n) 2,2-bis(4-methoxphenyl)-12-methoxy-10-oxo-2,10-dihydro[2]benzopyrano[4',3':3,4]naphtho(2,1-b)pyran;

o) 6-bis(4-methoxyphenyl)-12-methoxy-10-oxo-6,10-dihydro[2]benzopyrano[3',4':3,4]naphtho(1,2-b)pyran;

p) 6,6-diphenyl-9-oxo-6,9-dihydro[1]benzopyrano[3',4':3,4]naphtho(1,2-b)pyran; and q) 3,3-diphenyl-8-oxo-3,8-dihydro[2]benzopyrano[3',4':5,6]naphtho(2,1-b)pyran.

5. A photochromic article comprising a polymeric organic host material and a photochromic amount of the naphthopyran compound of claim 1.

6. The photochromic article of claim 5 wherein the polymeric organic host material is selected from the group consisting of poly($C_1$–$C_{12}$ alkyl methacrylates), poly(oxyalkylene dimethacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of bis(allyl carbonate) monomers, polyfunctional acrylate monomers, polyfunctional methacrylate monomers, diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers, alkoxylated polyhydric alcohol acrylate monomers, styrene monomers, urethane acrylate monomers, glycidyl acrylate monomers, glycidyl methacrylate monomers and diallylidene pentaerythritol monomers.

7. The photochromic article of claim 6 wherein the polymeric organic host material is a solid transparent polymer selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis(allyl carbonate) monomers, diethylene glycol dimethacrylate monomers, ethoxylated phenol bismethacrylate monomers, diisopropenyl benzene monomers and ethoxylated trimethylol propane triacrylate monomers.

8. The photochromic article of claim 7 wherein the photochromic compound is present in an amount of from 0.05 to 1.0 milligram per square centimeter of organic host material surface to which the photochromic substance(s) is incorporated or applied.

9. The photochromic article of claim 8 wherein said transparent polymer is an optical element.

10. The photochromic article of claim 9 wherein said optical element is a lens.

11. A photochromic article comprising a polymeric organic host material selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis(allyl carbonate) monomers, diethylene glycol dimethacrylate monomers, ethoxylated phenol bismethacrylate monomers, diisopropenyl benzene monomers and ethoxylated trimethylol propane triacrylate monomers, and a photochromic amount of the naphthopyran compound of claim 3.

12. A photochromic article comprising a polymerizate of an optical organic resin monomer and a photochromic amount of the naphthopyran compound of claim 1.

13. The photochromic article of claim 12 wherein the refractive index of the polymerizate is from about 1.48 to about 1.75.

14. The photochromic article of claim 13 wherein the refractive index of the polymerizate is from about 1.495 to about 1.66.

15. A photochromic article comprising, in combination, a solid transparent polymeric organic host-material, and a photochromic amount of each of (a) at least one naphthopyran compound of claim 1, and (b) at least one other organic photochromic compound having at least one activated absorption maxima within the range of between about 400 and 700 nanometers.

16. The photochromic article of claim 15 wherein the polymeric organic host material is selected from the group consisting of poly($C_1$–$C_{12}$ alkyl methacrylates), poly(oxyalkylene dimethacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of bis(allyl carbonate) monomers, polyfunctional acrylate monomers, polyfunctional methacrylate monomers, diethylene glycol dimethacrylate monomers, ethoxylated bisphenol A dimethacrylate monomers, diisopropenyl benzene monomers, ethylene glycol bismethacrylate monomers, poly(ethylene glycol) bismethacrylate monomers, ethoxylated phenol bismethacrylate monomers, alkoxylated polyhydric alcohol acrylate monomers, styrene monomers, urethane acrylate monomers, glycidyl acrylate monomers, glycidyl methacrylate monomers and diallylidene pentaerythritol monomers.

17. The photochromic article of claim 16 wherein the polymeric organic host material is a solid transparent homopolymer or copolymer selected from the group consisting of poly(methyl methacrylate), poly(ethylene glycol bis-methacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, ethoxylated phenol bismethacrylate monomers, diisopropenyl benzene monomers and ethoxylated trimethylol propane triacrylate monomers.

18. The photochromic article of claim 15 wherein the organic photochromic compound (b) is selected from the group consisting of other naphthopyrans, chromenes, oxazines, metal-dithizonates, fulgides and fulgimides.

19. The photochromic article of claim 18 wherein the total amount of photochromic compound present is from 0.05 to 1.0 milligram per square centimeter of organic host material surface to which the photochromic substance(s) is incorporated or applied.

20. The photochromic article of claim 18 wherein said transparent polymeric organic host material is an optical element.

21. The photochromic article of claim 20 wherein said optical element is a lens.

22. A photochromic article comprising, in combination, a polymeric organic host material selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, ethoxylated phenol bismethacrylate monomers, diisopropenyl benzene monomers and ethoxylated trimethylol propane triacrylate monomers, and a photochromic amount of each of (a) at least one naphthopyran compound of claim 3, and (b) at least one other organic photochromic compound having at least one activated absorption maxima within the range of between about 400 and 700 nanometers.

* * * * *